(12) United States Patent
Carobbi et al.

(10) Patent No.: US 6,214,124 B1
(45) Date of Patent: Apr. 10, 2001

(54) PROCESS FOR THE PREPARATION OF A LACTULOSE SYRUP BY LACTOSE ISOMERIZATION

(75) Inventors: Renato Carobbi, Pistoia; Giuseppe Bimbi, Pontedera; Giovanni Cipolletti, Milan, all of (IT)

(73) Assignee: Inalco S.P.A., Milan (IT)

( * ) Notice: Subject to any disclaimer, the term of this patent is extended or adjusted under 35 U.S.C. 154(b) by 0 days.

(21) Appl. No.: 09/402,768

(22) PCT Filed: Apr. 17, 1998

(86) PCT No.: PCT/EP98/02245

§ 371 Date: Oct. 11, 1999

§ 102(e) Date: Oct. 11, 1999

(87) PCT Pub. No.: WO98/47908

PCT Pub. Date: Oct. 29, 1998

(30) Foreign Application Priority Data

Apr. 17, 1997 (IT) .............................................. MI97A0889

(51) Int. Cl.⁷ .................................................... C13K 13/00

(52) U.S. Cl. ................................. 127/36; 127/46.2; 127/58
(58) Field of Search .................................. 127/36, 462, 58

(56) References Cited

U.S. PATENT DOCUMENTS 4,957,564 * 9/1990 Carobbi et al. ...................... 127/46.3

FOREIGN PATENT DOCUMENTS

| 0318630 | 6/1989 | (EP) . |
| 0320670 | 6/1989 | (EP) . |
| 0622374 | 11/1994 | (EP) . |

* cited by examiner

*Primary Examiner*—David Brunsman
(74) *Attorney, Agent, or Firm*—Hedman & Costigan, P.C.

(57) ABSTRACT

Process for the preparation of lactulose wherein an aqueous solution or suspension of lactose is reacted with sodium aluminate in order to produce the isomerization of lactose and the mixture thus obtained is neutralized by treatment with gaseous $CO_2$ under pressure, obtaining a suspension of aluminum hydroxide which can be easily separated from the lactulose solution.

9 Claims, No Drawings

PROCESS FOR THE PREPARATION OF A LACTULOSE SYRUP BY LACTOSE ISOMERIZATION

FIELD OF THE INVENTION

The present invention refers to an industrial process for the production of lactulose by isomerization of lactulose using sodium aluminate.

STATE OF THE ART

Lactulose is a synthetic disaccharide normally used in the form of a syrup for the treatment of intestinal disorders and in the form of crystalline product as sweetener substituent of saccarose. It is also used as food supplement in pediatric and geriatric diets.

Many processes for the preparation of lactulose by isomerization of lactose, which is a natural disaccharide widely available, are known.

Some of this processes are essentially based on the isomerization of lactose by strong bases as for example $Ca(OH)_2$, NaOH, KOH and strong organic bases.

These processes present the drawbacks that the sugars can be randomly degraded; such degradations cause a fall in the lactulose yield, complicate the extraction steps necessary to eliminate the degraded products, impoverish the syrups quality and make more difficult the preparation of crystalline lactulose. Another group of processes uses, as isomerizing agents, sodium tetraborate and sodium aluminate.

These processes, although allow to obtain higher yields of lactulose and a purer product, are not industrially acceptable for the difficulty presented by the necessary filtration of aluminum hydroxide and by the total elimination of boric acid.

Other processes, using strongly basic ion-exchange resins for the isomerization, are too much expensive and do not allow the production of lactulose at acceptable prices.

Processes for the isomerization of lactulose using magnesium compounds are also known.

These processes present the drawbacks to require very high reaction volumes for obtaining small quantities of lactulose.

An improved process is described in U.S. Pat. No. 4,957,564 wherein the isomerization of lactulose is obtained by catalysis with sodium aluminate followed by neutralization with sulphuric acid. However, in performing this process high quantities of sodium sulphate are produced and the elimination of this product implies ecological problems difficult and expensive to solve.

SUMMARY OF THE INVENTION

We have now found a process for the preparation of lactulose which allows to overcome the prior art problems.

In particular we have found a process for the isomerization of lactose to lactulose using sodium aluminate which allows an easy filtration of the aluminum hydroxide and its easy reconversion into the sodium aluminate to be used in the following cycle and moreover allows to avoid ecological problems.

The process according to the present invention comprises the following steps:
a) reaction of an aqueous solution or suspension of lactose with sodium aluminate in order to produce the isomerization of lactose to lactulose with a low conversion of lactose or with an high conversion of lactose;
b) quenching with ice of the mixture obtained in step (a);
c) neutralization of the mixture obtained in step (b) with precipitation of the aluminum hydroxide;
d) separation of the aluminum hydroxide by filtration;
e) deionisation of the solution obtained in step (d);
f1) concentration of the solution obtained in step (e) up to obtaining a technical syrup in the case of high conversion of lactose;
f2) concentration of the solution obtained in step (e) to be treated according to following step (i) in the case of low conversion of lactose;
g) treatment of the aluminum hydroxide obtained in step (d) with $NaHCO_3$, $Na_2CO_3$ or with NaOH, in the quantity necessary to convert the aluminum hydroxide into sodium aluminate;
h) calcination of the product from step (g) to obtain the sodium aluminate which is recycled in step (a);
i) crystallization from the solution of step (f2) of the non-isomerized lactose, which is recycled in step (a), this process being characterised by the fact that said low conversion of lactose is limited to 55–65%, said high conversion of lactose is comprised between 90 and 95% and said neutralization of step (c) is performed by treatment with gaseous $CO_2$ under pressure.

Besides the above mentioned advantages, by performing the process according to the present invention it is also possible to obtain a product having higher purity and with higher yield.

DETAILED DESCRIPTION OF THE INVENTION

The advantages and characteristics of the process for the preparation of lactulose by isomerization of lactose according to the present invention will be better illustrated in the following description.

According to the process for lactulose preparation of the present invention, first of all a solution or suspension of lactose in water is prepared, wit a lactose content of 20–50% by weight; said solution or suspension is warmed at temperature comprised between 25°–50° C.

To such lactose solution or suspension a solution of sodium aluminate (30%–40% by weight) is added, in few minutes an homogeneous solution is obtained which is reacted at a temperature comprised between 25–50° C. for 6–16 h.

The sodium aluminate is used with a molar ratio of 0.5:1–2:1 calculated on lactose.

The obtained mixture is poured on ice (30–40% by weight calculated on the mixture) in order to produce a quick cooling, to stop the transformation of lactose into lactulose and to inhibit all secondary reactions.

By stirring for 10–20 minutes an homogeneous solution having temperature 15–18° C. is obtained.

By following the above reported procedure and choosing the appropriated molar ratios between sodium aluminate and lactose and the reaction time and temperature, as described also in the following examples, it is possible to obtain a low lactose conversion, for example 55–65% with a lactulose yield of 83–85% or it is possible to obtain a high conversion of lactose, for example 90–95% with a lactulose yield of 68–75%. The homogeneous solution obtained as above described is continuously neutralized by treatment with gaseous $CO_2$ at 0.25–0.5 MPa at a temperature from 20° to 32°–35° C. for at least 1 h.

With this procedure a mixture consisting of a solution of lactulose and lactose containing dissoived $NaHCO_3$ and suspended aluminum hydroxide, is obtained. The obtained mixture after neutralization is filtered preferably by filter press.

The solid obtained by filtration, consisting essentially of aluminum hydroxide and sodium bicarbonate, is suspended in water and filtered again. The obtained liquid, consisting essentially of a solution of lactulose, lactulose and soluble salts, is deionized using ion-exchange resins according to known techniques and thereafter is concentrated up to a saccharimetric content of 60°–80° Brix.

The concentration is performed under reduced pressure (0.0026–0.0046 MPa) at a temperature of the concentrated solution of 45–50° C. or lower.

In the case of high lactose conversion, a technical, commercializable syrup is obtained.

In the case of low lactose conversion the concentrated mixture is cooled down under stirring at 20° C. and thereafter at 5–15° C. for 120–130 h, giving the crystallization of the lactose non-converted during the isomerization step.

The lactose is separated by centrifugation and the remaining liquid is a lactulose syrup having high purity, a lactulose concentration of 50–55% by weight and little quantities of other sugars like lactose and galactose.

The crystallized lactose, after washing with cold water at the end of the centrifugation, is recycled to the initial step as starting material for a new cycle. In step g) the solid from the filtration performed after neutralization, is mixed up with $NaHCO_3$, $Na_2CO_3$ or NaOH, added as solids or in aqueous solution, preferably as solids, in the appropriated quantity to obtain a sodium quantity useful for the production of sodium aluminate ($NaAlO_2$ or $Na_2O$—$Al_2O_3$) according to known techniques, for the production of aluminate (according to such techniques besides the stoichiometric quantity of sodium in respect of Al, it is necessary to add a further quantity in the form of a base containing sodium).

Normally the solid from the filtration performed after the neutralization, consisting essentially of aluminum hydroxide and sodium bicarbonate, is mixed with additional $NaHCO_3$, in the quantity useful to obtain the sodium quantity necessary to produce sodium aluminate; the obtained solid mixture is calcinated at 750°900° C. and the organic material is cracked giving the sodium aluminate which is recycled to the isomerization step.

In order to better illustrate the process according to the present invention the following examples are reported without limiting purposes. In the reported examples the term "Amberlite" is a registered trade mark.

EXAMPLE 1

To 2515 g of demineralised water 1750 g of white grade lactose were added (title 94.8%, 4.846 moles). The obtained suspension was warmed under stirring at 30° C. At that temperature 773 g (3.393 moles) of sodium aluminate (solution 36.5% by weight having free alkalinity, expressed as NaOH equivalent of 7.5% by weight) were added to the suspension. After few minutes the mass changed into a clear solution, having gold-yellow colour; the solution was left under stirring at the given temperature for 14 h, then was poured on 1774 g of ice; after 15 minutes stirring an homogeneous solution was obtained.

The analysis of the solution showed that 1005 g of lactose had been consumed and 852 g of lactulose had been produced with a conversion of 60.6% and a yield of 84.8%.

The solution was continuously neutralised treating with gaseous $CO_2$ under 0.35 Mpa at 25° C. in a "Buss" reactor at inverted saturation flux for 90 minutes.

The obtained mixture was filtered by filter press.

The obtained solid was suspended in water, filtered again, characterised in its analytical composition referring to the Al and $NaHCO_3$ contents and, following the results of the analysis, was mixed with the quantity of sodium bicarbonate necessary to form the sodium aluminate as requested by the known procedures. The obtained mixture was calcinated at 750° C. giving the reconverted sodium aluminate.

The liquid from filtration was deionized by ion-exchange resins according to known procedures (resins as Amberlite IR 120 or 200 C and resins as Amberlite IRA 94S). The liquid was concentrated under reduced pressure (0.0035 MPa), at a temperature of the concentrate of 40° C. up to a saccharimetric content of 71.4° Brix.

The liquid from the concentration step was cooled under stirring at 20° C. and thereafter at 10° C. for 125 h, thereby the lactose non converted during the isomerization crystallized.

By centrifugation a solid consisting of crystalline lactose was separated from a liquid consisting of a syrup having saccharimetric content of 61.8° Brix and a lactulose content of 53.2%, lactose 4% and galactose 2.2% (by weight) as determined by HPLC.

EXAMPLE 2

To 2874 g of demineralized water 2000 g of yellow grade lactose (title 94.5%, 5.521 moles) are added. The suspension was warmed under stirring at 30° C. At that temperature, 883 g (3.865 moles) of sodium aluminate (solution 36.5% by weight having free alkalinity, expressed as NaOH equivalent of 7.5% by weight) were added to the suspension. After few minutes the mass changed into a clear solution, having gold-yellow colour; the solution was left under stirring at the given temperature for 14 h, then was quickly poured on 2028 g of ice, obtaining, after 15 minutes stirring, an homogeneous solution.

The analysis of the solution showed that 1150 g of lactose had been consumed and 968 g of lactulose had been produced with a conversion of 61% and a yield of 84.2%.

The solution was continuously neutralized by treating with gaseous $CO_2$ under 0.33 Mpa at 26° C. in a "Buss" reactor at inverted saturation flux for 95 minutes.

The obtained mixture was filtered by filter press.

The obtained solid was suspended in water, filtered again, characterised in its analytical composition referring to the Al and $NaHCO_3$ contents and, following the results of the analysis, was mixed with the quantity of sodium bicarbonate necessary to form the sodium aluminate as requested by the known procedures. The obtained mixture was calcinated at 750° C. giving the reconverted sodium aluminate.

The liquid from filtration was deionized by ion-exchange resins according to known procedures (resins as Amberlite IR 120 or 200 C and resins as Amberlite IRA 94S). Therefore, the liquid was concentrated under reduced pressure (0.0030 MPa), at a temperature of the concentrate of 40° C. up to a saccharimetric content of 71.40 Brix.

The liquid from the concentration step was cooled under stirring, first at 20° C. and thereafter at 8° C. for 120 h, obtaining the crystallization of the lactose non converted during the isomerization.

By centrifugation a solid consisting of crystalline lactose was separated from a liquid consisting of a syrup having saccharimetric content of 61.7° Brix and a lactulose content of 52.4%, lactose 4.3% and galactose 2.5% (by weight) as determined by HPLC.

EXAMPLE 3

To 4188 g of demineralized water 2000 g of white grade lactose (title 94.8%, 2.517 moles) were added. The suspension was warmed under stirring at 30° C. and 860 g (3.304 moles) of sodium aluminate (solution 31.5% by weight having free alkalinity, expressed as NaOH equivalent of 5.0% by weight) were added to the suspension.

The obtained solution was warmed under stirring for 1 h up to 39° C. and these conditions were maintained for 11 hours, thereafter the solution was poured on 1200 g of ice; after 15 minutes stirring an homogeneous cold solution was obtained.

The analysis of the solution showed that 817 g of lactose had been consumed and 596 g of lactulose had been produced with a conversion of 94.8% and a yield of 73.0%.

The solution was continuously neutralised by treating with gaseous $CO_2$ under 0.35 Mpa at 25° C. in a "Buss" reactor at inverted saturation flux for 90 minutes.

The obtained mixture was filtered by filter press.

The obtained solid was suspended in water, filtered again, characterised in its analytical composition referring to the Al and $NaHCO_3$ contents and, following the results of the analysis, was mixed with the quantity of $NaHCO_3/Na_2CO_3$ necessary to form $NaAlO_2$.

The obtained mixture was calcinated at 750° C. giving, almost quantitatively, the reconverted sodium aluminate.

The liquid from the first and second filtration was deionized by ion-exchange resins according to known procedures (resins as Amberlite IR 120 or 200 C and resins as Amberlite IRA 94S).

The deionised solution was concentrated under reduced pressure (0.0035 MPa), at a temperature not exceeding 55° C. up to a saccharimetric content of 67.8° Brix. 1102 g of a syrup having a lactulose content of 51.4%, lactose 4.1% and galactose 4.0% by weight were recovered.

EXAMPLE 4

To 5170 g of lactose aqueous solution at 17.0% by weight warmed at 30° C., 850 g (3.298 moles) of sodium aluminate (solution 32% by weight having free alkalinity, expressed as NaOH equivalent of 6.2% by weight) were added.

The obtained solution was warmed under stirring for 1 h up to 39° C. and maintained at this temperature for other 11.5 hours, thereafter the solution was quickly poured on 1250 g of ice; after 15 minutes stirring a homogeneous cold solution was obtained.

The analysis of the solution showed that 844 g of lactose had been consumed and 586 g of lactulose had been produced with a lactose conversion of 96.0% and a lactulose yield of 69.5%.

The solution was continuously neutralized by treating with gaseous $CO_2$ under 0.35 MPa at 25° C. in a "Buss" reactor at inverted saturation flux for 90 minutes.

The obtained mixture was filtered by filter press.

The obtained solid was suspended in water, filtered again, characterised in its analytical composition referring to the Al and $NaHCO_3$ contents and, following the results of the analysis, was mixed with the quantity of $NaHCO_3/Na_2CO_3$ necessary to form $NaAlO_2$.

The obtained mixture was calcinated at 750° C. giving, almost quantitatively, the reconverted sodium aluminate.

The liquid from the first and second filtration was deionized by ion-exchange resins according to known procedures (resins as Amberlite IR 120 or 200 C and resins as Amberlite IRA 94S).

The deionised solution was concentrated under reduced pressure (0.0035 MPa), at a temperature not exceeding 55° C. up to a saccharimetric content of 68.2° Brix. 1080 g of a syrup having a lactulose content of 51.6%, lactose 3.3% and galactose 4.4% by weight were recovered.

What is claimed is:

1. Process for the preparation of a lactulose syrup by isomerization of lactose comprising the following steps:
    a) reaction of an aqueous solution or suspension of lactose with sodium aluminate in order to produce the isomerization of lactose to lactulose with a conversion of lactose limited to 55–65% or with conversion of lactose of between 90 and 95%;
    b) quenching with ice of the mixture obtained in step (a);
    c) neutralization of the mixture obtained in step (b) with precipitation of the aluminum hydroxide performed by treatment with gaseous $CO_2$ under pressure;
    d) separation of the aluminum hydroxide by filtration;
    e) deionization of the solution obtained in step (d);
    f1) concentration of the solution obtained in step (e) up to obtaining a technical syrup in the case of the conversion of lactose of between 90 and 95%;
    f2) concentration of the syrup obtained in step (e) to be treated according to the following step (i) in the case of conversion lactose limited to 55–65%
    g) treatment of the aluminum hydroxide obtain ed in step (d) with $NaHCO_3$, $Na_2CO_3$ or with NaOH, in the quantity necessary to convert the aluminum hydroxide into sodium aluminate;
    h) calcination of the product from step (g) to obtain the sodium aluminate which is recycled to step (a);
    i) crystallization from the solution of step (f2) of the non-isomerized lactose, which is recycled to step (a).

2. Process according to claim 1, wherein said aqueous solution or suspension of step (a) has a lactose content of 20–50% by weight.

3. Process according to claim 1, wherein said reaction step (a) is performed at 25°–50° C.

4. Process according to claim 1, wherein said reaction of step (a) is performed with a molar ratio of sodium aluminate/lactose of 0.5:1–2:1.

5. Process according to claim 1, wherein said quenching step (b) is performed by pouring the mixture obtained from step (a) on ice using an ice quantity of 30–40% (by weight) calculated on said mixture.

6. Process according to claim 1, wherein said neutralization according to step (c) is performed continuously with gaseous $CO_2$ at 0.25–0.5 MPa and 20°–35° C.

7. Process according to claim 1, wherein said concentration of steps (f1) and (f2) is performed at 0.0026–0.0046 MPa at a temperature not exceeding 45°–50° C.

8. Process according to claim 1, wherein said concentration of steps (f1) and (f2) is continued up to a saccharometric content of 60°–80° Brix.

9. Process according to claim 1, wherein said crystallization of step (i) is performed by cooling first at 20° C. and thereafter at 5°–15° C. for a total of 120–130 hours.

* * * * *